(12) United States Patent
Endo et al.

(10) Patent No.: US 7,433,733 B2
(45) Date of Patent: Oct. 7, 2008

(54) MOTION MEASUREMENT METHOD, MOTION MEASUREMENT SYSTEM, AND MOTION MEASUREMENT PROGRAM

(75) Inventors: Yosuke Endo, Wako (JP); Ritsuo Hara, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 264 days.

(21) Appl. No.: 11/154,238

(22) Filed: Jun. 16, 2005

(65) Prior Publication Data

US 2006/0004299 A1    Jan. 5, 2006

(30) Foreign Application Priority Data

Jun. 30, 2004    (JP)    ............................. 2004-194063

(51) Int. Cl.
  *A61B 5/04*    (2006.01)
  *A61B 5/117*    (2006.01)
  *A61B 5/103*    (2006.01)

(52) U.S. Cl. ...................................... 600/546; 600/595

(58) Field of Classification Search ................. 600/546, 600/587, 595
See application file for complete search history.

(56) References Cited

FOREIGN PATENT DOCUMENTS

| JP | 2001-286451 | 10/2001 |
|---|---|---|
| JP | 2003-089083 | 3/2003 |
| JP | 2003-116893 | 4/2003 |

*Primary Examiner*—Max Hindenburg
*Assistant Examiner*—Brian Szmal
(74) *Attorney, Agent, or Firm*—Rankin, Hill & Clark LLP

(57) ABSTRACT

A method, system, and program enabling a variable varying with an animal's motions to be accurately measured. First, a reference relational expression representing a relation between myoelectric potentials and motion is set on the basis of the myoelectric potentials and the variable measured by using an inverse dynamics model. Then, the motion variable is measured on the basis of the measured myoelectric potentials and according to the reference relational expression. A reference relational expression is set on the basis of myoelectric potentials measured in a first motion and a motion variable corresponding to the first motion. Then, a motion variable corresponding to a second motion is measured on the basis of the myoelectric potentials measured in the second motion and according to the reference relational expression.

9 Claims, 7 Drawing Sheets

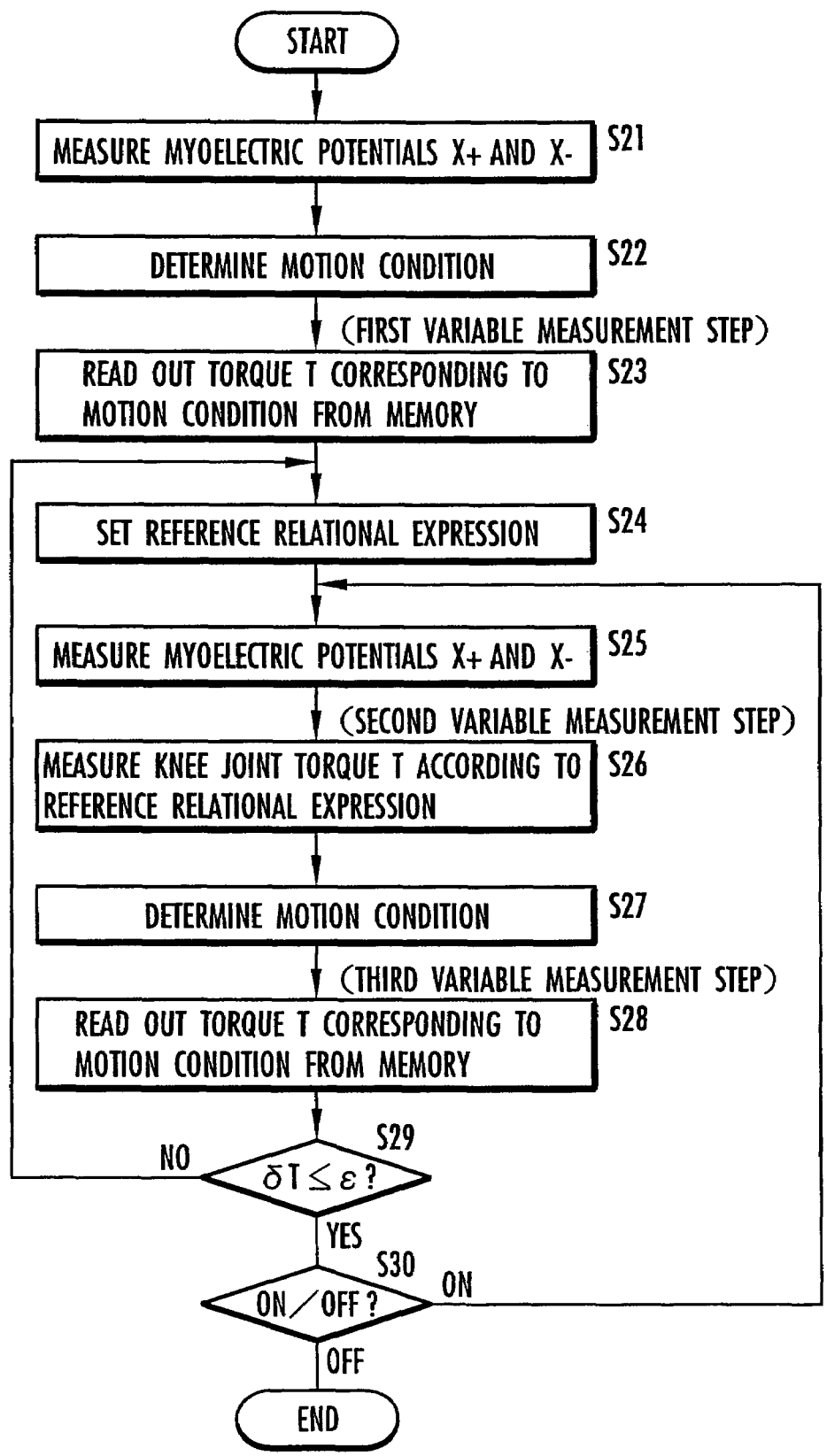

MOTION MEASUREMENT METHOD, MOTION MEASUREMENT SYSTEM, AND MOTION MEASUREMENT PROGRAM

BACKGROUND OF THE INVENTION

1. Field of the Invention

The present invention relates to a method of measuring animal's motions made by activities of muscle fibers, a system for measuring the animal's motions, and a program enabling a computer to have functions for measuring the animal's motions.

2. Related Background Art

There has been suggested a technology of measuring myoelectric signals generated in muscles of an animal including a human being and measuring a torque or the like of a joint of the animal based on the myoelectric signals (refer to, for example, Japanese Laid-Open Patent Publication (Kokai) No. 2001-286451). According to the related art, the myoelectric signals are measured, first, with given forces produced in a motion region of a subject, the plurality of myoelectric signals measured are translated to a plurality of pseudo tensile forces, and then the maximum value among the plurality of pseudo tensile forces is determined as a normalized reference value. Subsequently, the myoelectric signals with the forces produced in the motion region of the subject are measured, pseudo tensile forces are acquired based on the measured myoelectric signals and the previously determined normalized reference value, and a torque is calculated based on the acquired pseudo tensile forces. The normalized reference value becomes the basis for identifying a correspondence between the myoelectric signals and the torque and for acquiring the torque based on the myoelectric signals in the motion region.

According to the related art, however, the myoelectric signals are measured under the condition where given forces are sequentially produced in a plurality of directions in the motion region by following the sequence in which consideration is given to muscle activation in the motion region, whereby the normalized reference value is determined. Therefore, in order to determine the normalized reference value to be a basis for measuring the torque, the related art forces the subject to produce the given forces sequentially in the plurality of directions in the motion region at least once. Furthermore, if the correspondence between the myoelectric signals and the torque varies with variations in various conditions such as an increase in muscular fatigue, the subject is forced to produce given forces in a plurality of directions in the motion region again in order to determine the normalized reference value anew. As mentioned above, according to the related art, the subject is forced to make a given motion different from a series of his/her motions concerned before or in the middle thereof.

For example, if the related art is adopted to a device for assisting a man in walking by giving a torque corresponding to a leg torque generated by a walking man bending and stretching his hip joints or knee joints, he is forced to make a motion different from the walking motion such as bending and stretching of his knees or standing on one foot before or during walking. On the other hand, a man using a walking aid device due to his weak muscle cannot make the given motion with the weak muscle even if he is forced to make it. Thus, he is very likely to have an uncomfortable feeling.

SUMMARY OF THE INVENTION

Therefore, it is an object of the present invention to provide a method, system, and program for accurately measuring a variable varying with animal's motions such as a joint torque in a series of the animal's motions.

According to one aspect of the present invention which achieves the object related to a method of measuring motions of an animal made by activities of muscle fibers, comprising the steps of: myoelectric potential measurement for measuring myoelectric potentials generated in an animal's body; first variable measurement for measuring a variable varying with the animal's motions; reference relational expression setting for setting a reference relational expression representing a relation between the myoelectric potentials and the variable on the basis of the myoelectric potentials measured in the myoelectric potential measurement step and the variable measured in the first variable measurement step; and second variable measurement for measuring a variable intended to be measured in the first variable measurement step on the basis of the myoelectric potentials measured in the myoelectric potential measurement step and according to the reference relational expression set in the reference relational expression setting step.

According to this aspect of the present invention, first the reference relational expression representing the relation between the myoelectric potentials and the variable is set in the reference relational expression setting step on the basis of the myoelectric potentials measured in the myoelectric potential measurement step and the variable measured in the first variable measurement step. This method does not force the animal to make a given motion to set the reference relational expression. Thereafter, the variable measured in the first variable measurement step is measured in the second variable measurement step on the basis of the myoelectric potentials measured in the myoelectric potential measurement step and according to the reference relational expression. For example, if the animal makes arbitrary first and second motions continuously, a reference relational expression is set on the basis of myoelectric potentials measured in the first motion and a variable corresponding to the first motion, first. Then, a variable corresponding to the second motion is measured according to the reference relational expression on the basis of the myoelectric potentials measured in the second motion.

Therefore, according to the aspect of the present invention, it is possible to measure the variable accurately in the series of animal's motions after setting the reference relational expression without forcing the animal to make a given motion.

Furthermore, the motion measurement method of the present invention has a feature that the first variable measurement step includes measuring the variable according to an inverse dynamics model representing a behavior of the animal.

According to the above feature, the variable is measured according to the inverse dynamics model representing the animal's behavior in the first variable measurement step.

Still further, the motion measurement method of the present invention further comprises a motion condition determination step of determining a motion condition of the animal on the basis of the variable varying with the animal's motions, wherein the first variable measurement step includes measuring the variable on the basis of the motion condition determined in the motion condition determination step.

According to the above feature, the variable is measured according to the animal's motion condition in the first variable measurement step.

Furthermore, the motion measurement method of the present invention further comprises a third variable measurement step of measuring the variable intended to be measured in the second variable measurement step simultaneously with and separately from the second variable measurement step and a deviation determination step of determining whether a deviation between the variable measured in the second variable measurement step and the variable measured in the third variable measurement step exceeds a threshold, wherein the reference relational expression setting step includes setting a new reference relational expression on the basis of the myoelectric potentials measured in the myoelectric potential measurement step and the variable measured in the third variable measurement step if the deviation is determined to exceed the threshold in the deviation determination step.

According to the above feature, the deviation determination step includes determining whether the deviation between the variable measured according to the reference relational expression in the second variable measurement step and the variable measured simultaneously with and separately from the second variable measurement step in the third variable measurement step exceeds the threshold. The "deviation" includes a deviation at a single time point and an average deviation, a cumulative deviation, and the like at a plurality of time points or for a continuous time. If the deviation is determined to exceed the threshold, the new reference relational expression is set on the basis of the myoelectric potentials and the variable measured in the third variable measurement step. If the deviation exceeds the threshold, it is estimated that the relation between the myoelectric potentials and the variable expressed by the reference relational expression diverges from an actual relation therebetween due to a change in condition such as muscular fatigue or perspiration. The setting of the new reference relational expression, however, avoids the divergence. Moreover, the setting of the new reference relational expression does not force the animal to make a given motion. Therefore, even in an occurrence of a change in condition such as muscular fatigue or perspiration, the variable can be accurately measured according to the reference relational expression accurately representing the relation between the myoelectric potentials and the variable without forcing the animal to make a given motion.

Still further, the motion measurement method of the present invention has a feature that the third variable measurement step includes measuring the variable in the same method as in the first variable measurement step.

According to this feature, the reference relational expression and the new reference relational expression can be set on the basis of the variable measured in the same method.

Still further, the motion measurement method of the present invention has a feature that the reference relational expression setting step includes setting an equation between a pseudo variable as a myoelectric potential function and the variable as a reference relational expression.

According to this feature, the variable is measured (calculated) by determining the pseudo variable as the myoelectric potential function according to the reference relational expression.

Furthermore, the motion measurement method of the present invention has a feature that the reference relational expression setting step includes setting the reference relational expression so that the maximum value of the pseudo variable equals the maximum value of the variable.

According to the foregoing features, the variable is measured (calculated) by determining the pseudo variable as the myoelectric potential function according to the reference relational expression. Furthermore, the variable is measured (calculated) by normalizing the pseudo variable so that the maximum value of the pseudo variable equals the maximum value of the variable. The "maximum value" of the variable and that of the pseudo variable include the maximum value of the variable and that of the pseudo variable in a given time span and the maximum value of the variable and that of the pseudo variable in each period if the variable and the pseudo variable change periodically.

Still further, the motion measurement method of the present invention has a feature that the first and second variable measurement steps each include measuring a torque produced in a body part of the animal as a variable.

According to this feature, the torque produced in the body part of the animal is measured as the variable.

According to another aspect of the present invention which achieves the object related to a system for measuring motions of an animal made by activities of muscle fibers, comprising: myoelectric potential measurement means for measuring myoelectric potentials generated in an animal's body; first variable measurement means for measuring a variable varying with the animal's motions; reference relational expression setting means for setting a reference relational expression representing a relation between the myoelectric potentials and the variable on the basis of the myoelectric potentials measured by the myoelectric potential measurement means and the variable measured by the first variable measurement means; and second variable measurement means for measuring a variable intended to be measured by the first variable measurement means on the basis of the myoelectric potentials measured by the myoelectric potential measurement means and according to the reference relational expression set by the reference relational expression setting means.

According to this aspect of the present invention, it is possible to accurately measure the variable in a series of the animal's motions after setting the reference relational expression without forcing the animal to make a given motion.

According to still another aspect of the present invention which achieves the object related to a program enabling a computer to process functions for measuring motions of an animal made by activities of muscle fibers, the program enabling the computer to process: a myoelectric potential measurement function of measuring myoelectric potentials generated in an animal's body; a first variable measurement function of measuring a variable varying with the animal's motions; a reference relational expression setting function of setting a reference relational expression representing a relation between the myoelectric potentials and the variable on the basis of the myoelectric potentials measured by the myoelectric potential measurement function and the variable measured by the first variable measurement function; and a second variable measurement function of measuring a variable intended to be measured by the first variable measurement function on the basis of the myoelectric potentials measured by the myoelectric potential measurement function and according to the reference relational expression set by the reference relational expression setting function.

According to this aspect of the present invention, the computer can be provided with a function of accurately measuring the variable in a series of the animal's motions after setting the reference relational expression without forcing the animal to make a given motion.

BRIEF DESCRIPTION OF THE DRAWINGS

FIG. 7 is an explanatory diagram showing a motion measurement method according to the second embodiment of the present invention.

DETAILED DESCRIPTION OF THE PREFERRED EMBODIMENTS

The preferred embodiments of a motion measurement method, a motion measurement system, and a motion measurement program of the present invention will now be described in detail hereinafter with reference to the accompanying drawings.

Figure 1:
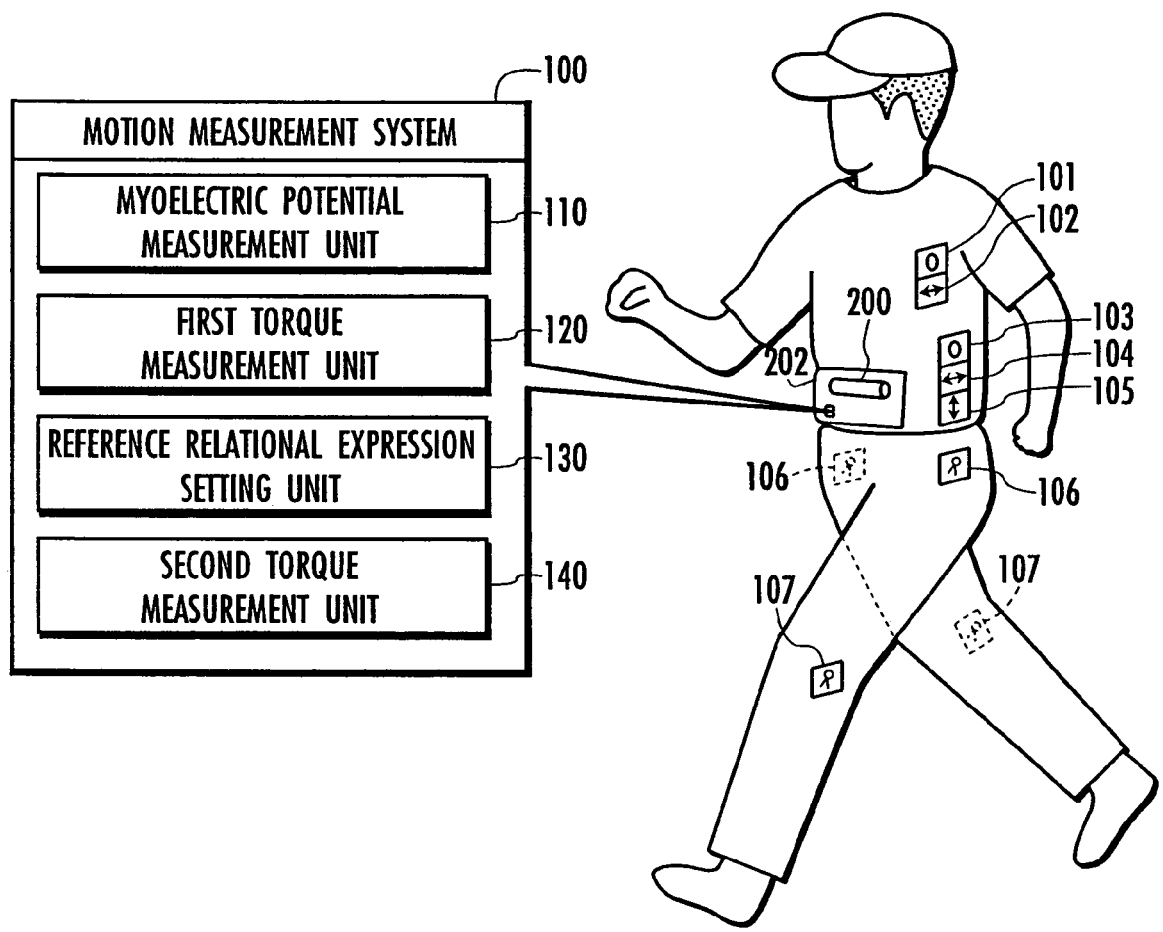
FIG. 1 is an explanatory configuration diagram showing a motion measurement system according to a first embodiment.
Figure 2:
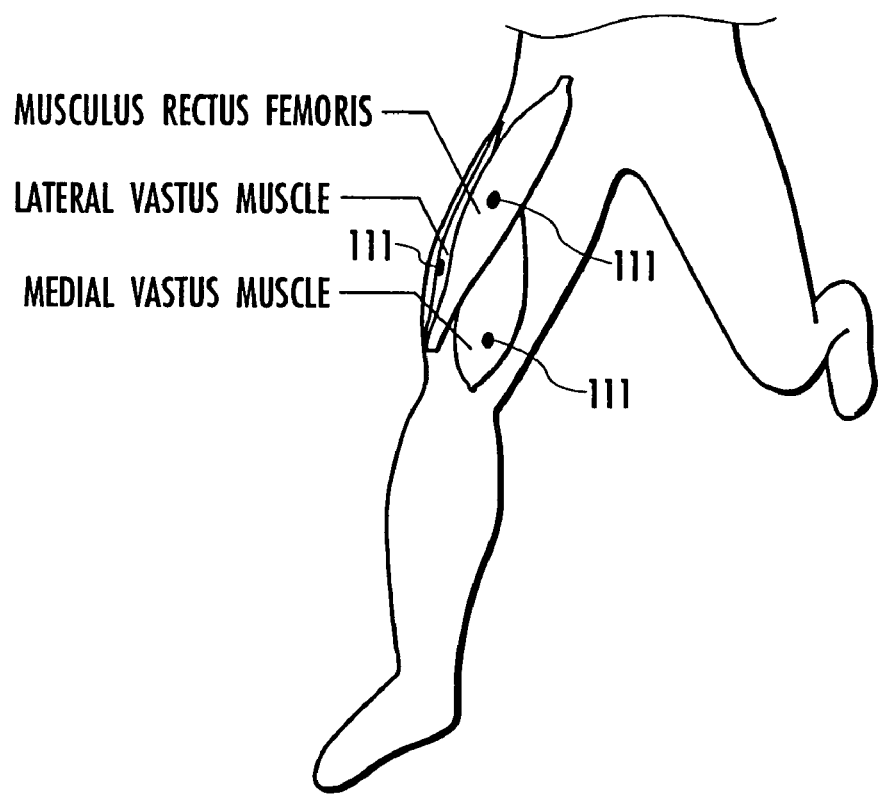
FIG. 2(a) is an explanatory diagram showing myoelectric potential measurement using surface electrodes on the extensor side.
FIG. 2(b) is an explanatory diagram showing myoelectric potential measurement using surface electrodes on the flexor side.
Figure 2:
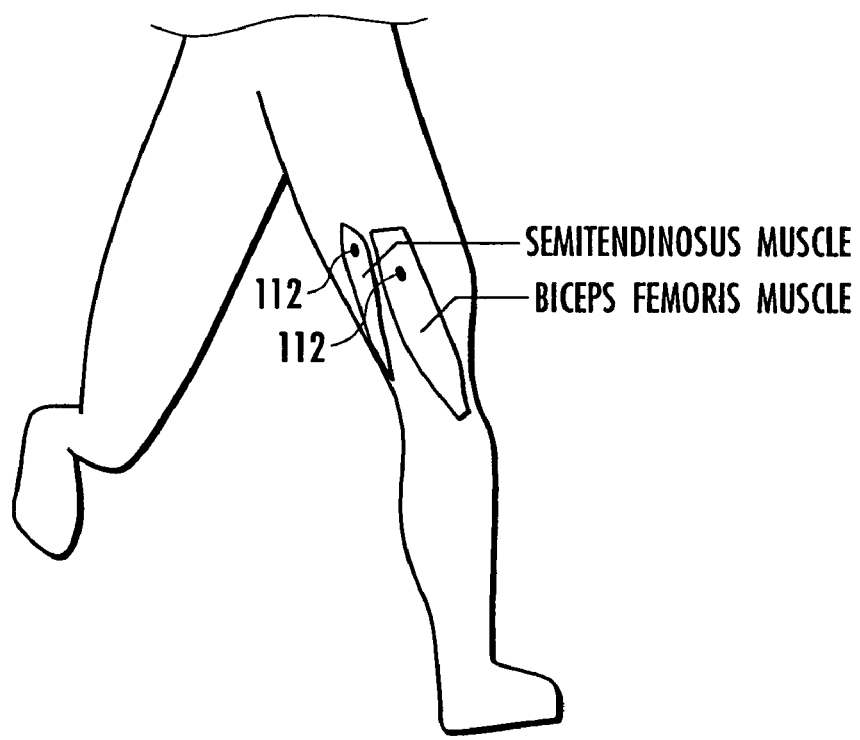
Figure 3:
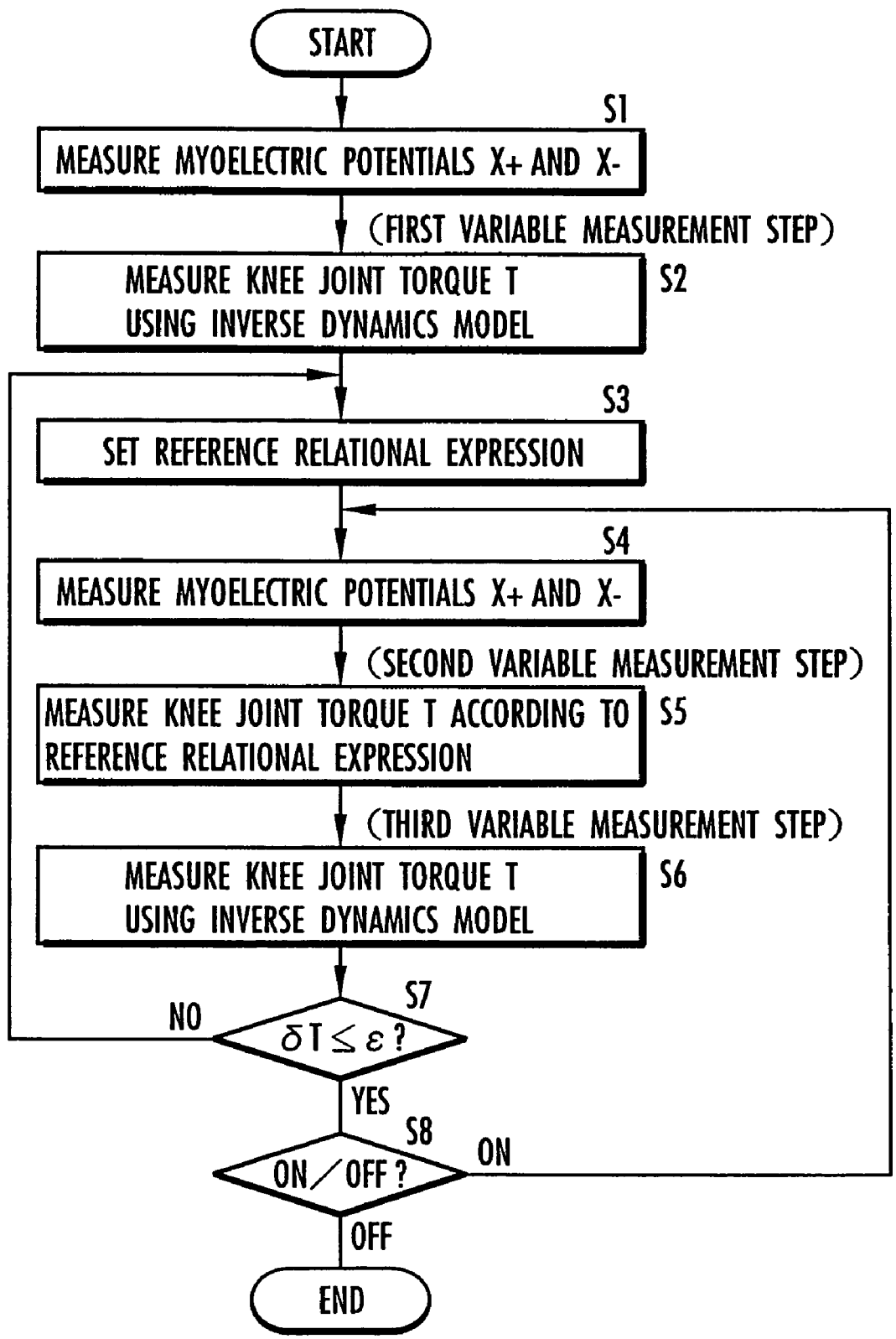
FIG. 3 is an explanatory diagram showing a motion measurement method according to the first embodiment of the present invention.
Figure 4:
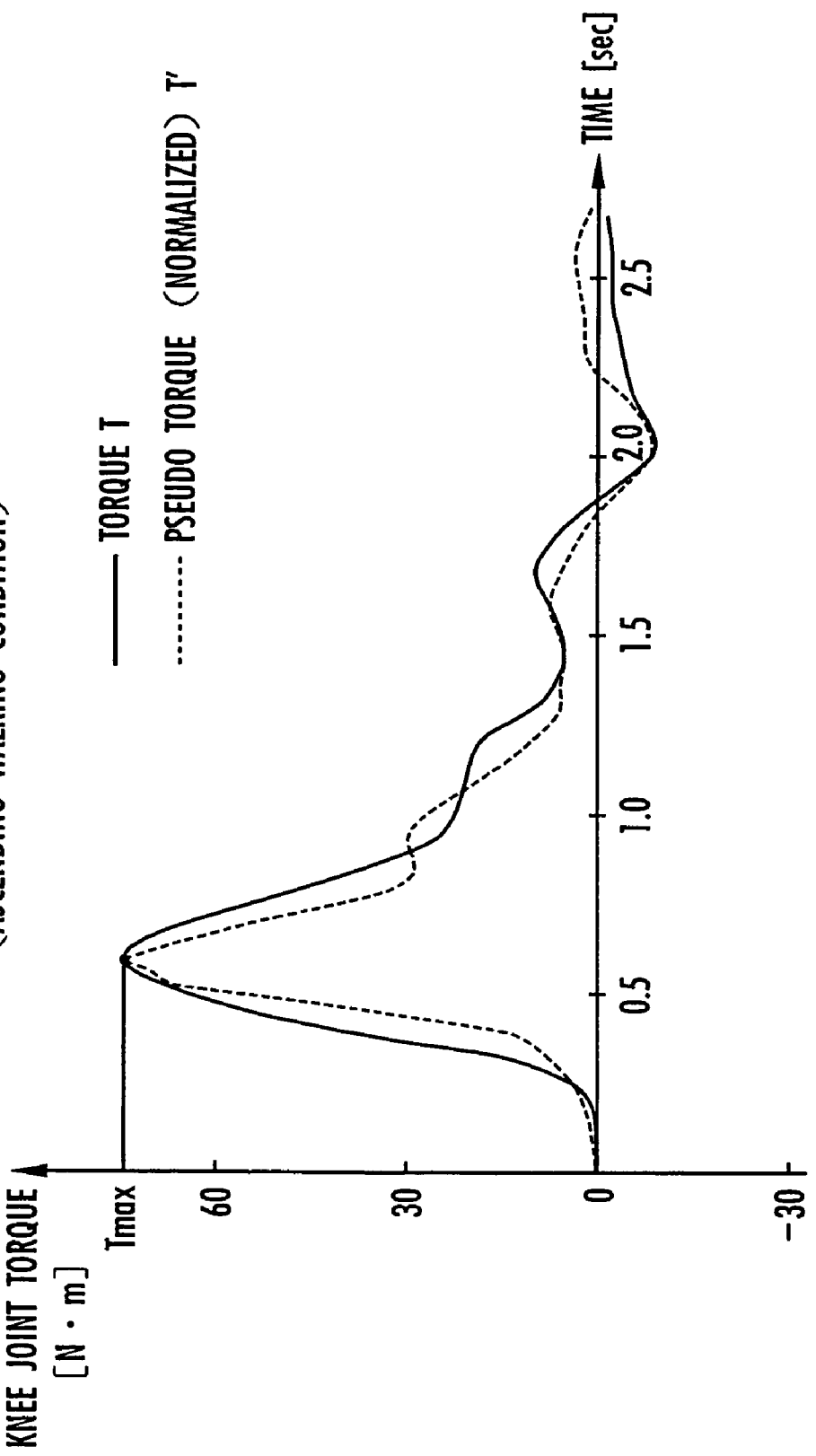
FIG. 4 is an explanatory diagram showing normalization of a pseudo variable with a variable in an ascending walking condition.
Figure 5:
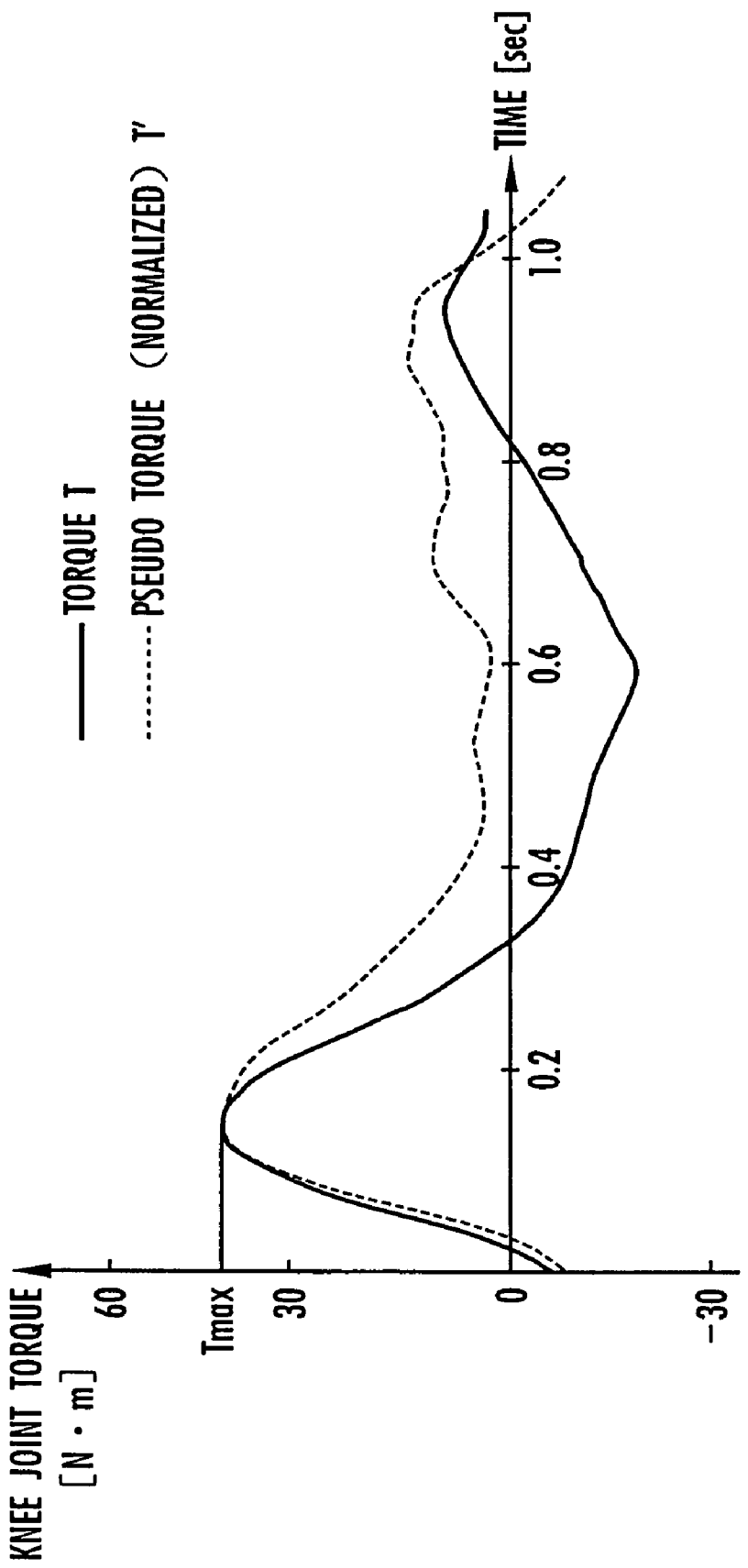
FIG. 5 is an explanatory diagram showing normalization of a pseudo variable with a variable in a level walking condition.
Figure 6:
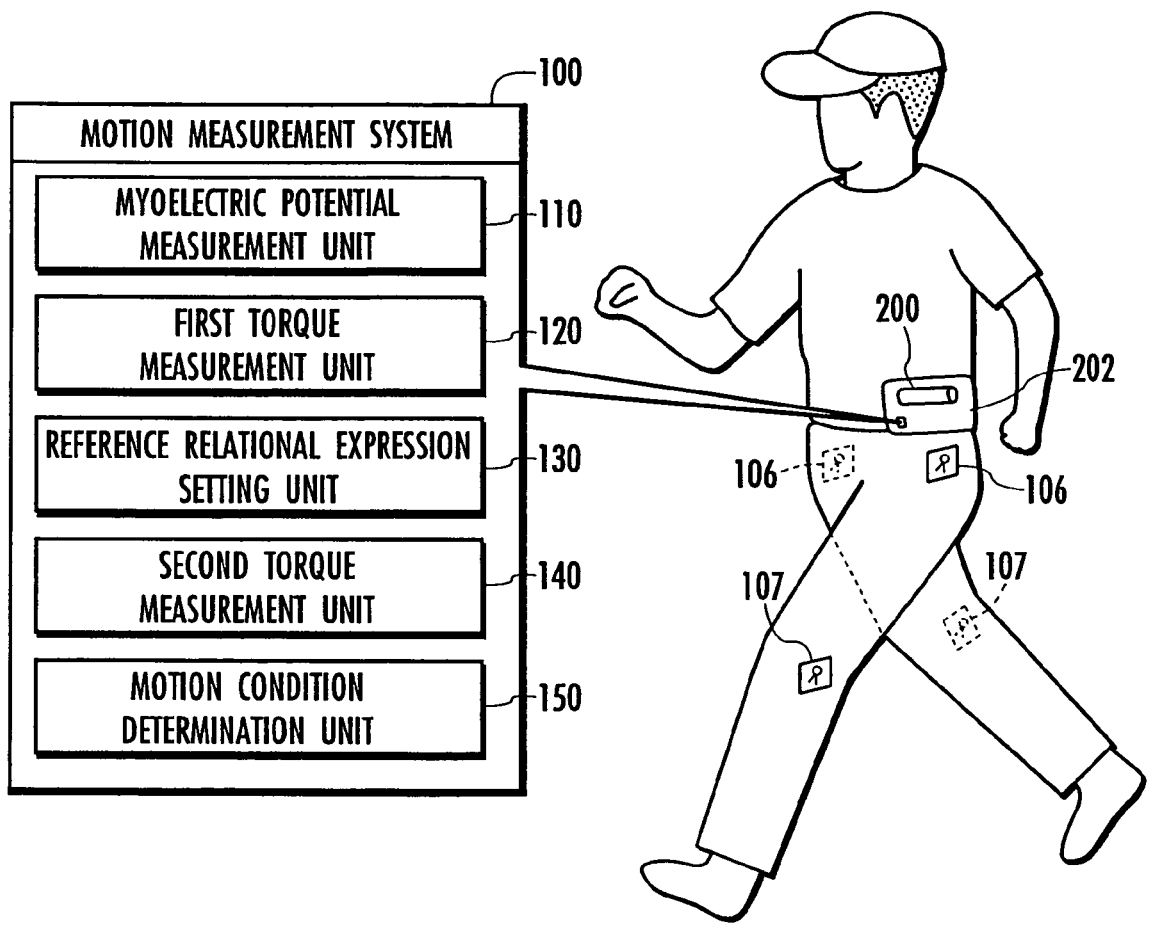
FIG. 6 is an explanatory configuration diagram of a motion measurement system according to a second embodiment of the present invention.

FIG. 1 shows an explanatory configuration diagram of a motion measurement system according to a first embodiment. FIGS. 2(a) and 2(b) show explanatory diagrams of a myoelectric potential measurement method. FIG. 3 shows an explanatory diagram of a motion measurement method according to the first embodiment of the present invention. FIG. 4 shows an explanatory diagram of normalization of a pseudo variable with a variable in an ascending walking condition. FIG. 5 shows an explanatory diagram of normalization of a pseudo variable with a variable in a level walking condition. FIG. 6 shows an explanatory configuration diagram of a motion measurement system according to a second embodiment of the present invention. FIG. 7 shows an explanatory diagram of a motion measurement method according to the second embodiment of the present invention.

First, the motion measurement system according to the first embodiment of the present invention will be described by using FIGS. 1 to 5.

A motion measurement system 100 shown in FIG. 1 is for use in measuring motions of a human being (an animal). The motion measurement system 100 comprises a chest gyro sensor 101 for outputting a signal according to a tilt angular velocity of a human chest whose motions are to be measured, a chest fore-and-aft acceleration sensor 102 for outputting a signal corresponding to a fore-and-aft acceleration of the chest, a lumbar gyro sensor 103 for outputting a signal corresponding to a tilt angular velocity of a lumbar, a lumbar fore-and-aft acceleration sensor 104 for outputting a signal corresponding to a fore-and-aft acceleration of the lumbar, a lumbar vertical acceleration sensor 105 for outputting a signal corresponding to a vertical acceleration of the lumbar, a hip joint angle sensor 106 for outputting a signal corresponding to a flexion angle of a hip joint, and a knee joint angle sensor 107 for outputting a signal corresponding to a flexion angle of a knee joint.

The motion measurement system 100 includes a myoelectric potential measurement unit 110, a first torque measurement unit (first variable measurement means) 120, a reference relational expression setting unit 130, and a second torque measurement unit (second variable measurement means) 140. Each unit is formed by a microcomputer including a CPU, a ROM, a RAM, and the like as hardware and "a motion measurement program" of the present invention stored in a memory as software. The microcomputer, which is a part of each unit, operates using a battery 200 as a power supply. It contains the battery and is housed in a body-worn case 202.

The myoelectric potential measurement unit 110 measures myoelectric potentials through surface electrodes 111 on the extensor side attached to regions of a medial vastus muscle, a lateral vastus muscle, and a musculus rectus femoris (extensor) on the surface of the human body as shown in FIG. 2(a) and through surface electrodes 112 on the flexor side attached to regions of a semitendinosus muscle and a biceps femoris muscle (flexor) as shown in FIG. 2(b). A first torque measurement unit 120 measures a knee joint torque by using an inverse dynamics model representing a human behavior on the basis of outputs from sensors 101 to 107.

A reference relational expression setting unit 130 sets "a reference relational expression" representing a relation between the myoelectric potentials and the knee joint torque on the basis of the myoelectric potentials measured by the myoelectric potential measurement unit 110 and the knee joint torque measured by the first torque measurement unit 120. Moreover, the reference relational expression setting unit 130 determines whether a deviation between the knee joint torque measured by the first torque measurement unit 120 and the knee joint torque measured by the second torque measurement unit 140 exceeds a threshold. If it determines that the deviation exceeds the threshold, it sets a new reference relational expression on the basis of the myoelectric potentials measured by the myoelectric potential measurement unit 110 and the knee joint torque measured by the first torque measurement unit 120.

The second torque measurement unit 140 measures the knee joint torque on the basis of the myoelectric potentials measured by the myoelectric potential measurement unit 110 and according to the reference relational expression set by the reference relational expression setting unit 130.

A motion measurement method executed by the motion measurement system 100 having the above configuration will be described below with reference to FIGS. 3 to 5. This motion measurement is started by switching an ON/OFF switch (not shown) attached to the case 202 from OFF to ON.

The myoelectric potential measurement unit 110 measures an extensor potential xi+ (i=1 (medial vastus muscle), 2 (lateral vastus muscle), 3 (musculus rectus femoris)) and a flexor potential xj− (j=1 (semitendinosus muscle), 2 (biceps femoris muscle)) through the surface electrodes 111 on the extensor side and the surface electrodes 112 on the flexor side (S1). The extensor potential xi+ and the flexor potential xj− are generated by activities of muscle fibers and vary with a human walking motion or the like. The extensor potential xi+ and the flexor potential xj− measured by the myoelectric potential measurement unit 110 are obtained by passing myoelectric signals, which have been detected by the surface electrodes 111 on the extensor side and the surface electrodes 112 on the flexor side, through a filter and an amplifier, A/D-converting the myoelectric signals, deriving absolute values therefrom, and passing them through a low-pass filter.

Furthermore, the first torque measurement unit 120 measures a knee joint torque T (corresponding to "a first variable measurement step" in S2) on the basis of outputs from the sensors 101 to 107 made by human motions and by using an inverse dynamics model representing a human behavior. Specifically, the first torque measurement unit 120 measures (estimates) the knee joint torque T on the basis of: a chest tilt angle and fore-and-aft acceleration; a lumber tilt angle, fore-and-aft acceleration, and vertical acceleration; a hip joint angle; and a knee joint angle. As for a concrete measurement method of the knee joint torque using the inverse dynamics model, for example, the method disclosed in Japanese Laid-Open Patent Publication (Kokai) No. 2003-89083 may be adopted, and its detailed description is omitted in this specification. The knee joint torque T is defined with the direction of extension of the knee joint, namely the direction of moving each lower leg forward, as a positive direction.

Furthermore, the reference relational expression setting unit 130 sets a reference relational expression between the extensor potential xi+ and the flexor potential xj− measured by the myoelectric potential measurement unit 110 and the knee joint torque T measured by the first torque measurement unit 120 for each motion condition determined by the motion condition determination unit 150 (S3).

Specifically, as expressed by the following equation (1), an equation between the knee joint torque T measured using the inverse dynamics model by the first torque measurement unit 120 and a pseudo torque T' as a function of the extensor potential x+ and the flexor potential x− measured by the myoelectric potential measurement unit 110 is set as a reference relational expression:

$$T=T'(xi+, xj-) \quad (1)$$

The pseudo torque T' as the function of the extensor potential x+ and the flexor potential x− is defined by the following equation (2):

$$T'=\Sigma i=1 \text{ to } 3 ci+xi+MAi++\Sigma i=1, 2cj-xj-MAj- \quad (2)$$

where ci+ and cj− are coefficients having signs reversed from each other, wherein a ratio between them is set, for example, as expressed by ci+:cj−=1:−⅓; and MAi+ is a moment arm of the extensor, namely a distance between a rotation center of the joint and a position where the extensor adheres to a bone, varying with the flexion angle of the joint. Likewise, MAj− is a moment arm of the flexor, namely a distance between a rotation center of the joint and a position where the flexor adheres to a bone, varying with the flexion angle of the joint. The extensor moment arm MAi+ and the flexor moment arm MAj− may be assumed to be equal to each other.

The coefficients ci+ and cj− are determined so that the maximum value Tmax of the knee joint torque T measured by the first torque measurement unit 120 equals the maximum value Tmax' of the pseudo torque T'. This normalizes (changes in scale) the pseudo torque T' so that the maximum value Tmax of the knee joint toque T (indicated by a solid line) equals the maximum value Tmax' of the pseudo torque (indicated by a dashed line), for example, as shown in FIG. 4 and FIG. 5. FIG. 4 shows a joint torque T (solid line) and a normalized pseudo torque (dashed line) T' in "an ascending walking condition" in which a man is walking up stairs or a slope. FIG. 5 shows a joint torque T (solid line) and a normalized pseudo torque (dashed line) T' in "a level walking condition" in which a man is walking on level ground.

If an extensor potential x+ is measured for one of a plurality of extensors and a flexor potential x− is measured for one of a plurality of flexors, the pseudo torque T' may be defined by the following equation (3):

$$T'=c+x+MA++c-x-MA- \quad (3)$$

If myoelectric potentials are measured for one extensor and a plurality of flexors or vice versa, the pseudo torque T' may be defined by the following equations (4) and (5):

$$T'=\Sigma ici+xi+MAi++c-x-MA- \quad (4)$$

$$T'=c+x+MA++\Sigma jcj-xj-MAj- \quad (5)$$

Thereafter, the myoelectric potential measurement unit 110 measures the extensor potential xi+ and the flexor potential xj− (S4). Then, the second torque measurement unit 140 measures the knee joint torque T on the basis of the extensor potential x+ and the flexor potential x− measured by the myoelectric potential measurement unit 110 and according to the reference relational expression corresponding to the motion condition determined by the reference relational expression setting unit 130 (see the equations (1) and (2)) (S5; corresponds to "a second variable measurement step").

Furthermore, the first torque measurement unit 120 measures the knee joint torque T by using the inverse dynamics model on the basis of outputs from the sensors 101 to 107 (S6; corresponds to a third variable measurement step).

Moreover, the reference relational expression setting unit 130 determines whether the deviation δT between the knee joint torque T (S5) measured by the second torque measurement unit 140 and the knee joint torque T (S6) measured by the first torque measurement unit 120 exceeds a threshold E or not (S7; corresponds to a deviation determination step). The deviation δT may be either a deviation between the maximum values of the both knee joint torques or an average deviation or a cumulative deviation for a certain period of time of the both knee joint torques.

If the reference relational expression setting unit 130 determines that the deviation δT exceeds the threshold ε (NO in S7), it sets a new reference relational expression (S3) by resetting the coefficients ci+ and cj− of the equation (2) on the basis of the knee joint torque T measured by using the inverse dynamics model (S6) and the extensor potential xi+ and the flexor potential xj− measured by the myoelectric potential measurement unit 110 (S4). Thereafter, the second torque measurement unit 140 measures the knee joint torque T according to the new reference relational expression (S5).

On the other hand, if the reference relational expression setting unit 130 determines that the deviation δT does not exceed the threshold ε (YES in S7) and the ON/OFF switch (not shown) remains to be set on (ON in S8), it does not set the new reference relational expression. In this condition, the second torque measurement unit 140 measures the knee joint torque T according to the existing reference relational expression (S5). If the ON/OFF switch is set off (OFF in S8), the subsequent processing such as myoelectric potential measurement or knee joint torque measurement is terminated.

According to the motion measurement method executed by the motion measurement system 100, for example, if a human being (animal) makes arbitrary first and second motions continuously, a reference relational expression is set on the basis of myoelectric potentials (xi+ and xj−) measured in the first motion and the knee joint torque (variable) T corresponding to the first motion (S1 to S3), first. Then, the knee joint torque T corresponding to the second motion is measured according to the reference relational expression on the basis of myoelectric potentials (xi+ and xj−) measured in the second motion following the first motion (S4 and S5).

Therefore, it is possible to accurately measure the knee joint torque T in a series of motions of a human being (animal) after setting the reference relational expression without forcing the human being to make a given motion.

If the deviation δT between the knee joint torque T (S5) measured according to the reference relational expression and the knee joint torque T (S6) measured simultaneously with and separately therefrom exceeds the threshold ε (NO in S7), a new reference relational expression is set (S3) on the basis of the myoelectric potentials (S4) and the knee joint torque T (S6).

If the deviation $\delta T$ exceeds the threshold $\epsilon$, it is estimated that the relation between the myoelectric potentials (xi+ and xj−) and the knee joint torque T represented by the reference relational expression diverges from an actual relation therebetween due to a change in condition such as muscular fatigue or perspiration. The setting of the new reference relational expression, however, avoids the divergence. In addition, the human being is not forced to make a given motion to set the new reference relational expression. Therefore, even if a change in condition such as muscular fatigue or perspiration occurs, it is possible to measure the knee joint torque T accurately according to the reference relational expression accurately representing the relation between the myoelectric potentials (xi+ and xj−) and the knee joint torque T without forcing the human being to make a given motion.

The following describes a motion measurement system according to a second embodiment of the present invention with reference to FIG. 6 and FIG. 7.

A configuration of the motion measurement system of the second embodiment of the present invention will now be described with reference to FIG. 6. A motion measurement system 100 of the second embodiment shown in FIG. 6 does not include the chest gyro sensor 101, the chest fore-and-aft acceleration sensor 102, the lumbar gyro sensor 103, the lumbar fore-and-aft acceleration sensor 104, and the lumbar vertical acceleration sensor 105. On the other hand, it is the same in the configuration as the motion measurement system of the first embodiment shown in FIG. 1 and FIG. 2 except that it additionally includes a motion condition determination unit 150. Therefore, the same reference numerals are retained for the same parts and their description is omitted here.

The motion condition determination unit 150 determines a human motion condition on the basis of an output from a hip joint angle sensor 106 and an output from a knee joint angle sensor 107.

A motion measurement method executed by the motion measurement system 100 having the foregoing configuration will be described by using FIG. 7. The motion measurement method of the second embodiment is substantially the same as the motion measurement method of the first embodiment except that a motion condition determined by the motion condition determination unit 150 is used instead of the inverse dynamics model in "the measurement of the knee joint torque T" in the first and third variable measurement steps.

A myoelectric potential measurement unit 110 measures an extensor potential xi+ and a flexor potential xj− through surface electrodes 111 on the extensor side and surface electrodes 112 on the flexor side (S21).

Moreover, the motion condition determination unit 150 measures a human motion condition on the basis of outputs from the hip joint angle sensor 106 and the knee joint angle sensor 107 (S22). As for a concrete determination method of the motion condition, for example, the method disclosed in Japanese Laid-Open Patent Publication (Kokai) No. 2003-116893 may be adopted, and its detailed description is omitted in this specification. By using the method, the motion condition determination unit 150 determines which human motion condition is applicable out of a plurality of motion conditions such as "a level walking condition" in which a man is walking on a level ground or a vanishingly gentle slope, "a descending walking condition" in which he is walking down stairs or a slope, "an ascending walking condition" in which he is walking up stairs or a slope, "a rising-from-chair condition" in which he is rising from a chair, and "a sitting-on-chair condition" in which he is sitting on a chair from the stand up position.

Furthermore, the first torque measurement unit 120 reads out (measures) a knee joint torque T stored in a memory (not shown) according to the corresponding motion condition on the basis of the motion condition determined by the motion condition determination unit 150 (S23; corresponds to "a first variable measurement step"). For example, if the motion condition determination unit 150 determines the condition to be "the ascending walking condition," the first torque measurement unit 120 reads out (measures) a knee joint torque T, as indicated by a solid line in FIG. 4, previously stored in the memory so as to correspond to the ascending walking condition. If the motion condition determination unit 150 determines the condition to be "the level walking condition," the first torque measurement unit 120 reads out (measures) a knee joint torque T, as indicated by a solid line in FIG. 5, previously stored in the memory so as to correspond to the level walking condition.

In addition, the reference relational expression setting unit 130 sets a reference relational expression between the extensor potential xi+ and the flexor potential xj− measured by the myoelectric potential measurement unit 110 and the knee joint torque T measured by the first torque measurement unit 120 for each motion condition determined by the motion condition determination unit 150 (S24).

Thereafter, the myoelectric potential measurement unit 110 measures the extensor potential xi+ and the flexor potential xj− (S25). Then, the second torque measurement unit 140 measures the knee joint torque T on the basis of the extensor potential x+ and the flexor potential x− measured by the myoelectric potential measurement unit 110 and according to the reference relational expression corresponding to the motion condition determined by the reference relational expression setting unit 130 (S26; corresponds to "a second variable measurement step").

The motion condition determination unit 150 determines the user motion condition on the basis of outputs from the hip joint angle sensor 106 and the knee joint angle sensor 107 (S27). Furthermore, the first torque measurement unit 120 reads out (measures) the knee joint torque T stored in the memory (not shown) on the basis of the motion condition determined by the motion condition determination unit 150 corresponding to the motion condition (S28; corresponds to "a third variable measurement step").

The reference relational expression setting unit 130 determines whether the deviation $\delta T$ between the knee joint torque T (S26) measured by the second torque measurement unit 140 and the knee joint torque T (S28) measured by the first torque measurement unit 120 exceeds the threshold $\epsilon$ (S29; corresponds to "a deviation determination step").

If the reference relational expression setting unit 130 determines that the deviation $\delta T$ exceeds the threshold $\epsilon$ (NO in S29), it sets a new reference relational expression (S24) by resetting the coefficients ci+ and cj− in the equation (2) on the basis of the knee joint torque T (S28) and the extensor potential xi+ and the flexor potential xj− (S25) measured by the myoelectric potential measurement unit 110. Thereafter, the second torque measurement unit 140 measures the knee joint torque T according to the new reference relational expression (S26).

On the other hand, if the reference relational expression setting unit 130 determines that the deviation $\delta T$ does not exceed the threshold $\epsilon$ (YES in S29) and the ON/OFF switch (not shown) remains to be set on (ON in S30), it does not set a new reference relational expression. In this condition, the second torque measurement unit 140 measures the knee joint torque T according to the existing reference relational expression (S26). If the ON/OFF switch is set off (OFF in S30), the subsequent processing such as myoelectric potential measurement or knee joint torque measurement is terminated.

According to the motion measurement method executed by the motion measurement system 100, it is also possible to accurately measure the knee joint torque T in a series of motions of a human being (animal) after setting the reference relational expression without forcing the human being to make a given motion. Moreover, in case of a change in condition such as muscular fatigue or perspiration, the knee joint torque T can be accurately measured according to the reference relational expression accurately representing the relation between the myoelectric potentials ($xi+$ and $xj-$) and the knee joint torque T without forcing the human being to make a given motion.

While the animal whose motions are measured has been a human being in the above embodiments, it can be any of all kinds of animals that make motions with activities of muscle fibers such as a monkey, a giraffe, or any other mammal or a fish as an alternative.

While the knee joint torque has been measured as a variable in the above embodiments, the variable to be measured may be a joint torque other than the knee joint torque, such as a hip joint torque, an ankle joint torque, a cubital joint torque, and a shoulder joint torque, or a joint angle, a joint angular velocity, a joint angular acceleration, and a rate of change in joint torque of a knee joint or the like as an alternative.

While the joint torque has been measured by using the inverse dynamics model on the basis of the output from the knee joint angle sensor 107 in the first embodiment and the joint torque has been measured on the basis of the motion condition determined based on the output from the knee joint angle sensor 107 in the second embodiment, the variable of the joint torque or the like may be measured in various methods such as, for example, in which a computer (not shown) measures the variable such as the joint torque on the basis of an after image of a camera (not shown) after the camera images human behaviors as an alternative.

While the coefficients $ci+$ and $cj-$ of the reference relational expression (See the equations (1) and (2)) have been determined so that the maximum value Tmax of the torque T equals the maximum value Tmax' of the pseudo torque T' in the above embodiment, the coefficients $ci+$ and $cj-$ of the reference relational expression may be determined so as to minimize an average deviation or a cumulative deviation at a plurality of time points or for a certain period of time of the torque T and the pseudo torque T' as an alternative.

While the torque (variable) measurement method in the first variable measurement step (S2 in FIG. 3 and S23 in FIG. 7) is identical with that in the third variable measurement step (S6 in FIG. 3 and S26 in FIG. 7) in the above embodiments, the torque measurement methods in the both steps may be different from each other as an alternative.

In the second embodiment, the coefficients $ci+$ and $cj-$ (see the equations (1) and (2)) and thus the reference relational expression may be set according to the motion condition determined by the motion condition determination unit 150. According to this embodiment, the torque or other variables can be more accurately measured according to the optimum reference relational expression corresponding to a user's (human being's) motion condition.

What is claimed is:

1. A method of measuring motions of an animal made by activities of muscle fibers, comprising the steps of:

a first myoelectric potential measurement step for measuring, by electrodes adapted to be attached to an animal's body, first myoelectric potentials generated in the animal's body;

a first variable measurement step for measuring, based on outputs from sensors adapted to be attached to the animal's body, a motion variable varying with the animal's motions;

a reference relational expression setting step for setting a reference relational expression representing a relation between the myoelectric potentials and the motion variable based on the first myoelectric potentials measured in the first myoelectric potential measurement step and the motion variable measured in the first variable measurement step;

a second myoelectric potential measurement step for measuring, by said electrodes attached to the animal's body, second myoelectric potentials generated in the animal's body, following said reference relational expression setting step; and a second variable measurement step for newly measuring said motion variable based on the myoelectric potentials measured in the second myoelectric potential measurement step and according to the reference relational expression set in the reference relational expression setting step.

2. The motion measurement method according to claim 1, wherein the first variable measurement step includes measuring the motion variable according to an inverse dynamics model representing a behavior of the animal.

3. The motion measurement method according to claim 1, further comprising a motion condition determination step of determining a motion condition of the animal based on the motion variable varying with the animal's motions, wherein the first variable measurement step includes measuring the motion variable based on the motion condition determined in the motion condition determination step.

4. The motion measurement method according to claim 1, further comprising the steps of:

a third variable measurement step of measuring, based on the outputs from the sensors attached to the animal's body, the motion variable intended to be newly measured in the second variable measurement step simultaneously with and separately from the second variable measurement step; and a deviation determination step of determining whether a deviation between the motion variable newly measured in the second variable measurement step and the motion variable measured in the third variable measurement step exceeds a threshold, wherein the reference relational expression setting step includes setting a new reference relational expression based on the myoelectric potentials measured in the myoelectric potential measurement step and the variable measured in the third variable measurement step if the deviation is determined to exceed the threshold in the deviation determination step.

5. The motion measurement method according to claim 1, wherein the reference relational expression setting step includes setting an equation between a pseudo variable as a myoelectric potential function and the motion variable as a reference relational expression.

6. The motion measurement method according to claim 5, wherein the reference relational expression setting step includes setting the reference relational expression so that the maximum value of the pseudo variable equals the maximum value of the motion variable.

7. The motion measurement method according to claim 1, wherein the first and second variable measurement steps each include measuring a torque produced in a body part of the animal as a variable.

8. A system for measuring motions of an animal made by activities of muscle fibers, comprising:
- a myoelectric potential measurement means for measuring, by electrodes adapted to be attached to an animal's body, myoelectric potentials generated in the animal's body;
- a first variable measurement means for measuring, based on outputs from sensors adapted to be attached to the animal's body, a motion variable varying with the animal's motions;
- a reference relational expression setting means for setting a reference relational expression representing a relation between the myoelectric potentials and the motion variable based on the myoelectric potentials measured by the myoelectric potential measurement means and the motion variable measured by the first variable measurement means; and
- a second variable measurement means for measuring, following the reference relation expression being set by the reference relational expression setting means, a second motion variable based on second myoelectric potentials measured by the myoelectric potential measurement means and according to the reference relational expression.

9. An article of manufacture comprising a program readable by a computer and embodying one or more instructions executable by the computer to perform a method of processing functions for measuring motions of an animal made by activities of muscle fibers, comprising:
- a myoelectric potential measurement function of measuring, by electrodes adapted to be attached to the animal's body, myoelectric potentials generated in an animal's body;
- a first variable measurement function of measuring a motion variable varying with the animal's motions on a basis of outputs from sensors adapted to be attached to the animal's body;
- a reference relational expression setting function of setting a reference relational expression representing a relation between the myoelectric potentials and the motion variable based on the myoelectric potentials measured by the myoelectric potential measurement function and the motion variable measured by the first variable measurement function; and
- a second variable measurement function of measuring a variable based on the myoelectric potentials measured by the myoelectric potential measurement function and according to the reference relational expression, following the reference relation expression being set by the reference relational expression setting means.

* * * * *